US012280360B2

(12) United States Patent
Luo et al.

(10) Patent No.: US 12,280,360 B2
(45) Date of Patent: Apr. 22, 2025

(54) CATALYST SYSTEMS AND METHODS FOR PRODUCING OLEFINS USING THE SAME

(71) Applicant: Dow Global Technologies LLC, Midland, MI (US)

(72) Inventors: Lin Luo, Freeport, TX (US); Yang Yang, Freeport, TX (US); Matthew T. Pretz, Freeport, TX (US)

(73) Assignee: Dow Global Technologies LLC, Midland, MI (US)

( * ) Notice: Subject to any disclaimer, the term of this patent is extended or adjusted under 35 U.S.C. 154(b) by 188 days.

(21) Appl. No.: 18/257,909

(22) PCT Filed: Dec. 15, 2021

(86) PCT No.: PCT/US2021/063480
§ 371 (c)(1),
(2) Date: Jun. 16, 2023

(87) PCT Pub. No.: WO2022/132876
PCT Pub. Date: Jun. 23, 2022

(65) Prior Publication Data
US 2024/0100510 A1 Mar. 28, 2024

Related U.S. Application Data

(60) Provisional application No. 63/127,435, filed on Dec. 18, 2020.

(51) Int. Cl.
*B01J 23/62* (2006.01)
*B01J 35/40* (2024.01)
*C07C 5/32* (2006.01)

(52) U.S. Cl.
CPC .............. *B01J 23/62* (2013.01); *B01J 35/40* (2024.01); *C07C 5/325* (2013.01);
(Continued)

(58) Field of Classification Search
CPC ... B01J 23/62; B01J 35/40; B01J 21/02; B01J 21/063; B01J 21/066; B01J 21/08;
(Continued)

(56) References Cited

U.S. PATENT DOCUMENTS 2,459,444 A   1/1949  Main
4,225,531 A * 9/1980  Jones ...................... B01J 8/32
                                                         201/31
(Continued)

FOREIGN PATENT DOCUMENTS

WO   2013126210 A1   8/2013
WO   2020006270 A2   1/2020
(Continued)

OTHER PUBLICATIONS

International Search Report and Written Opinion dated Apr. 4, 2022, pertaining to Int'l Patent Application No. PCT/US2021/063489.
(Continued)

*Primary Examiner* — Ali Z Fadhel
(74) *Attorney, Agent, or Firm* — Dinsmore & Shohl LLP

(57) ABSTRACT

According to one or more embodiments of the present disclosure, a fluidization promoter useful for dehydrogenation includes from 0.1 wt. % to 10 wt. % gallium, from 5 ppm to 500 ppm platinum, less than 5 wt. % alkali metal or alkaline earth metal, and a support material. A median particle size of the fluidization promoter is from 20 μm to 50 μm. Catalyst systems useful for dehydrogenation and methods for producing olefins using the same are also disclosed.

15 Claims, 1 Drawing Sheet

(52) U.S. Cl.
CPC ...... *C07C 2523/08* (2013.01); *C07C 2523/42* (2013.01); *C07C 2523/62* (2013.01)

(58) Field of Classification Search
CPC ... B01J 23/96; B01J 37/02; B01J 38/02; B01J 38/12; C07C 5/325; C07C 2523/08; C07C 2523/42; C07C 2523/62; C07C 5/3332; C07C 5/3335; C07C 5/3337; C07C 11/04; C07C 11/06; C07C 11/08; Y02P 20/52; Y02P 20/584
See application file for complete search history.

(56) References Cited

U.S. PATENT DOCUMENTS

| | | | |
|---|---|---|---|
| 7,473,668 | B2 | 1/2009 | Bartolini et al. |
| 7,959,792 | B2 | 6/2011 | Vaarkamp et al. |
| 9,815,040 | B2 | 11/2017 | Pretz et al. |
| 9,827,543 | B2 | 11/2017 | Pretz et al. |
| 9,834,496 | B2 | 12/2017 | Pretz et al. |
| 10,646,854 | B2 | 5/2020 | Iezzi et al. |
| 2014/0371501 | A1 | 12/2014 | Luo et al. |
| 2020/0002271 | A1* | 1/2020 | Chi ................. C07C 253/24 |

FOREIGN PATENT DOCUMENTS

| | | | |
|---|---|---|---|
| WO | 2020009860 | A1 | 1/2020 |
| WO | 2020009863 | A1 | 1/2020 |

OTHER PUBLICATIONS

International Search Report and Written Opinion dated Apr. 4, 2022, pertaining to Int'l Patent Application No. PCT/US2021/063481.
International Search Report and Written Opinion dated Apr. 5, 2022, pertaining to Int'l Patent Application No. PCT/US2021/063480.
Zabetakis, "Flammability Characteristics of Combustible Gases and Vapors", 627 Bureau of Mines (1965).
Coward et al., "Limits of Flammability of Gases and Vapors", 503 Bureau of Mines (1952).
Marceau et al., Impregnation and Drying, Synthesis of Solid Catalysts 59 (2008).
Cocco et al., Jet Cup Attrition Testing, 200 Powder Technology 224 (2010).
Smoothflow™ FCC additive—The solution for FCC fluidization and circulation problems https://www.albemarle.com/storage/wysiwyg/mib-smoothflow-final.pdf.
Marceau et al. "Impregnation and Drying", Synthesis of Solid Catalysts, pp. 59-78 (2009).
Abstract for "Additives Play Important Role in FCC Development", Oil and Gas Journal, Oct. 2012.
Abrahamsen et al. "Behavior of Gas-Fluidized Beds of Fine Powders: Part I. Homogeneous Expansion", Powder Technology, 1980, 26, pp. 35-46.
Abrahamsen et al. "Behavior of Gas-Fluidized Beds of Fine Powders: Part II. Voidage of the Dese Phase in Bubbling Beds", Powder Technology, 1980, 26, pp. 47-55.
Mott "Troubleshooting FCC Standpipe Flow Problems", Catalagram 106, 2009, pp. 11-20.

* cited by examiner

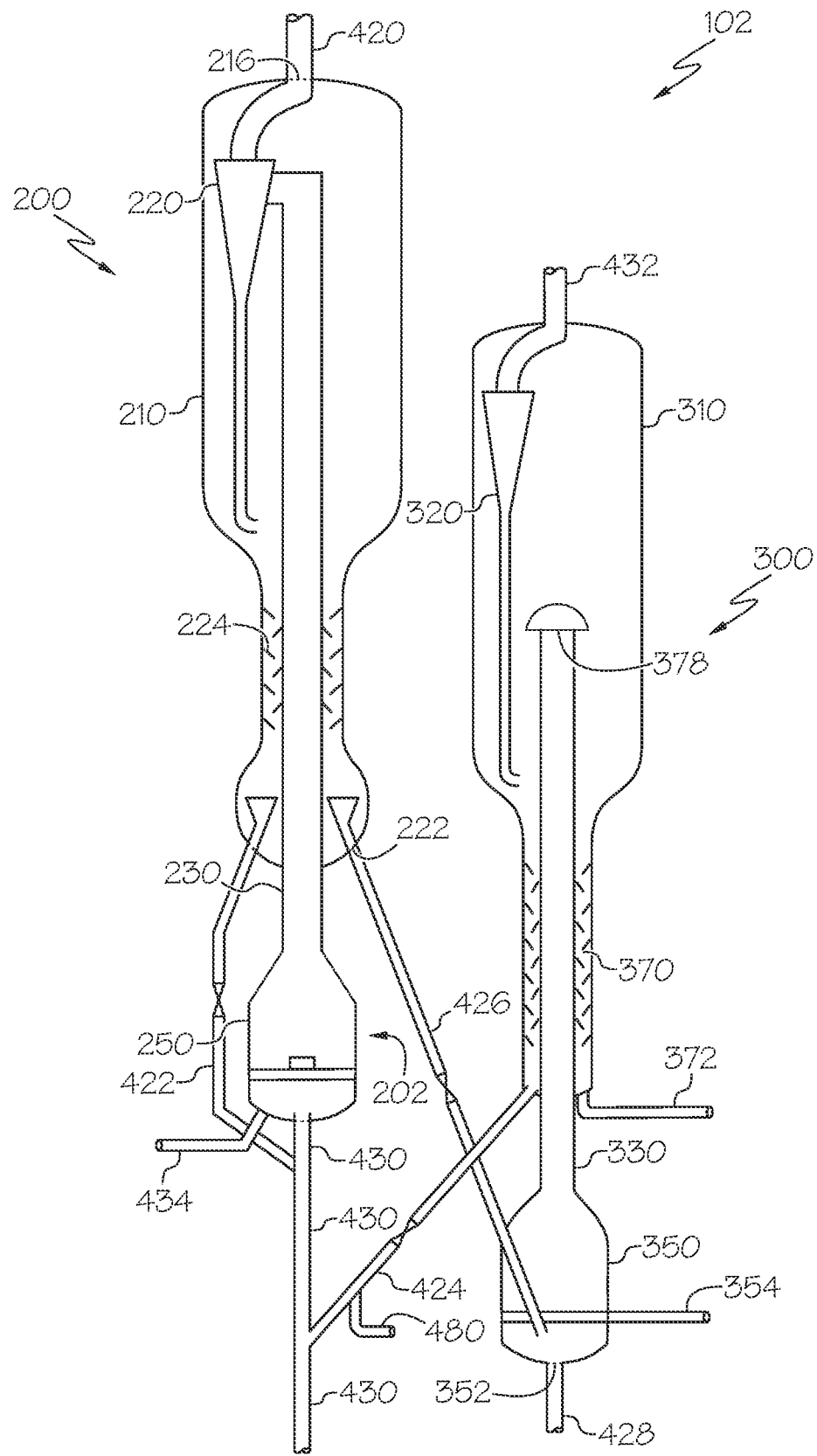

CATALYST SYSTEMS AND METHODS FOR PRODUCING OLEFINS USING THE SAME

CROSS-REFERENCE TO RELATED APPLICATIONS

The present application is a National Phase Entry under 35 U.S.C. § 371 of International Patent Application No. PCT/US2021/063480 filed Dec. 15, 2021, which claims priority to U.S. Provisional Patent Application No. 63/127,435 filed Dec. 18, 2020, the entireties of both of which are incorporated by reference herein.

BACKGROUND

Field

The present disclosure generally relates to chemical processing and, more specifically, catalyst systems and methods for producing olefins using the same.

Technical Background

Light olefins, such as ethylene, may be used as base materials to produce many different materials, such as polyethylene, vinyl chloride, and ethylene oxide, which may be used in product packaging, construction, and textiles. As a result of this utility, there is a worldwide increasing demand for light olefins. Suitable processes for producing light olefins generally depend on the given chemical feed and include, for example, fluidized catalytic dehydrogenation (FCDh) processes.

SUMMARY

Generally, the performance of FCDh systems is greatly dependent on the quality of fluidization of the catalyst. For example, the poor fluidization of the catalyst in a reactor portion of an FCDh system may lead to the formation of large bubbles of chemical feed. These bubbles allow for significant portions of the chemical feed to pass through the reactor portion without contacting the catalyst, which results in a reduced conversion rate. Similarly, poor fluidization of the catalyst in a catalyst-processing portion of the FCDh system may lead to poor contact with combustion fuel and, as a result, a reduced combustion performance. In order to improve the quality of fluidization of the catalyst, fluidization promoters may be mixed with the catalyst before introduction into the FCDh system and/or added to the FCDh system during operation. Ideally, fluidization promoters improve fluidization of the catalyst without negatively affecting the operation of the system. As a result, the selection of fluidizations promoter is heavily dependent on the properties of the reaction process and/or the catalyst. Based on this, some fluidization promoters are chemically inert particles that are added to the catalyst in an amount sufficient to achieve a desired quality of fluidization of the catalyst. However, these chemically inert particles dilute the average amount of catalytically active material in the system and, as a result, reduce the catalytic activity of the catalyst and/or conversion rate of the FCDh system. However, the catalyst systems and methods for producing olefins of the present disclosure may increase the quality of the fluidization of the catalyst while also maintaining a sufficient catalytic activity. This is accomplished, at least in part, by the utilization of a fluidization promoter that also provides catalytic activity.

According to one or more embodiments of the present disclosure, a fluidization promoter useful for dehydrogenation includes from 0.1 weight percent (wt. %) to 10 wt. % gallium, from 5 parts per million (ppm) to 500 ppm platinum, less than 5 wt. % alkali metal or alkaline earth metal, and a support material. The mean particle size of the fluidization promoter is from 20 microns (μm) to 50 μm.

According to one or more embodiments of the present disclosure, a catalyst system useful for dehydrogenation includes from 70 volume percent (vol. %) to 98 vol. % of a catalyst having a median particle size of from 50 μm to 90 μm and from 2 vol. % to 30 vol. % of a fluidization promoter having a median particle size of from 20 μm to 50 μm. The catalyst may include platinum, gallium, and a support material. The fluidization promoter may include platinum, gallium, and a support material. The fluidization promoter may include less platinum than the catalyst.

According to one or more embodiments of the present disclosure, a method for producing olefins includes contacting a hydrocarbon-containing feed with a catalyst in a reactor portion of a reactor system to form an olefin-containing effluent, separating at least a portion of the olefin-containing effluent from the catalyst, passing the catalyst to a catalyst-processing portion of the reactor system and processing the catalyst to produce a processed catalyst, passing the processed catalyst from the catalyst processing portion to the reactor portion, and introducing a fluidization promoter to the reactor system such that the quality of fluidization of the catalyst is improved. The catalyst may have a median particle size of from 50 μm to 90 μm and include platinum, gallium, and a support material. The fluidization promoter may have a median particle size of from 20 μm to 50 μm and include platinum, gallium, and a support material. The fluidization promoter may include less platinum than the catalyst.

It is to be understood that both the preceding general description and the following detailed description describe various embodiments and are intended to provide an overview or framework for understanding the nature and character of the claimed subject matter. Additional features and advantages of the embodiments will be set forth in the detailed description and, in part, will be readily apparent to persons of ordinary skill in the art from that description, which includes the accompanying drawing and claims, or recognized by practicing the described embodiments. The drawing is included to provide a further understanding of the embodiments and, together with the detailed description, serves to explain the principles and operations of the claimed subject matter. However, the embodiment depicted in the drawing is illustrative and exemplary in nature, and not intended to limit the claimed subject matter.

BRIEF DESCRIPTION OF THE DRAWINGS

The following detailed description may be better understood when read in conjunction with the following drawing, in which:

FIG. 1 schematically depicts a reactor system, according to one or more embodiments of the present disclosure.

When describing the simplified schematic illustration of FIG. 1, the numerous valves, temperature sensors, electronic controllers, and the like, which may be used and are well known to a person of ordinary skill in the art, are not included. Further, accompanying components that are often included in such reactor systems, such as air supplies, heat exchangers, surge tanks, and the like are also not included.

However, it should be understood that these components are within the scope of the present disclosure.

Reference will now be made in greater detail to various embodiments, some of which are illustrated in the accompanying drawing.

DETAILED DESCRIPTION

The present disclosure is directed to catalyst systems and methods for producing olefins using the same. More specifically, the present disclosure is directed to catalyst systems useful for dehydrogenation and methods for producing olefins via FCDh processes using the same. As discussed previously, the performance of fluidized bed reactors is greatly dependent on the quality of the fluidization of the catalyst. For example, the poor fluidization of the catalyst in a reactor portion of an FCDh system may lead to the formation of large bubbles of chemical feed. These bubbles allow for significant portions of the chemical feed to pass through the reactor portion without contacting the catalyst, which results in a reduced conversion rate. Similarly, the poor fluidization of the catalyst in a catalyst-processing portion of the FCDh system may lead to poor contact with combustion fuel and, as a result, reduced combustion performance.

An index commonly used to quantify the fluidization and describe the hydrodynamic behavior of a catalyst is the ratio $U_{mb}/U_{mf}$, where $U_{mb}$ is the minimum bubbling velocity and $U_{mf}$ is the minimum fluidization velocity of the catalyst. $U_{mb}/U_{mf}$ is also referred to as the maximum stable expansion ratio (MSER) of the catalyst. Generally, if the MSER of the catalyst is greater than 1, the catalyst will behave as Geldart Group A (i.e., the catalyst will fluidize relatively easy). Additionally, the greater the MSER of the catalyst is, the more "A-like" the fluidization behavior of the catalyst becomes. As a result, the catalyst is more forgiving to changes in density and readily circulate throughout the system.

The MSER of a catalyst may be determined using formula (I):

$$MSER = \frac{U_{mb}}{U_{mf}} = \frac{2300\rho_g^{0.126}\mu^{0.523}\exp(0.716F)}{d_p^{0.8}g^{0.934}(\rho_p - \rho_g)^{0.934}}$$

As noted above, $U_{mb}$ is the minimum bubbling velocity and $U_{mf}$ is the minimum fluidization velocity of the catalyst. $\rho_p$ is the particle density of the catalyst in kilograms per cubic meter (kg/m$^3$). $\rho_g$ is the density of the gas passing through the catalyst in kg/m$^3$, $\mu$ is the viscosity of the gas passing through the catalyst in kilograms per meter-second (kg/m·s). F is the weight fraction of the catalyst having a particle size of from 0 μm to 45 μm, $d_p$ is the Sauter Mean Diameter of the catalyst in meters (m). g is the gravitational acceleration constant (i.e., 9.81 meters per second squared (m/s$^2$)). The Sauter Mean Diameter of a catalyst may be determined using formula (II):

$$\bar{d}_p = \frac{1}{\sum \frac{x}{d_p}}$$

where x is the volume fraction of the catalytically active particles with the particle diameter $d_p$. It should be understood that the Sauter Mean Diameter is the diameter of a sphere that has the same volume to surface area ratio as a particle of interest. As Sauter Mean Diameter is more sensitive to particles having relatively small diameters, it is typically much lower than the median particle diameter derived from laser diffraction methods, such as ASTM D4464-15.

While MSER is a function of multiple variables, it is believed that the weight fraction of the catalyst having a particle size of from 0 μm to 45 μm (i.e., F) generally has the greatest impact on MSER. Additionally, it is believed that while all catalyst having a particle size less than 45 μm improve fluidization in theory, catalyst having a particle size less than 20 μm are too small to be retained in a FCDh system long enough to meaningfully affect fluidization.

In order to improve the quality of fluidization of the catalyst, fluidization promoters may be mixed with the catalyst before introduction into the FCDh system and/or added to the FCDh system during operation. Ideally, fluidization promoters improve fluidization of the catalyst without negatively affecting the operation of the FCDh system. As a result, the selection of fluidization promoters is heavily dependent on the properties of the reaction process and/or the catalyst. Based on this, some fluidization promoters are chemically inert particles that are added to the catalyst in an amount sufficient to achieve a desired quality of fluidization of the catalyst. However, these chemically inert particles dilute the average amount of catalytically active material in the system and, as a result, reduce the catalytic activity of the catalyst and/or conversion rate of the FCDh system.

As used in the present disclosure, the term "fluidized reactor system" refers to a reactor system in which one or more reactants are contacted with a catalyst in a fluidization regime, such as bubbling regime, slug flow regime, turbulent regime, fast fluidization regime, pneumatic conveying regime, or combinations of these, in different portions of the system. For example, in a fluidized reactor system, a chemical feed containing one or more reactants may be contacted with the circulating catalyst at an operating temperature to conduct a continuous reaction to produce an effluent.

As used in the present disclosure, the term "deactivated catalyst" refers to a catalyst having decreased catalytic activity resulting from buildup of coke and/or loss of catalyst active sites. The terms "catalytic activity" and "catalyst activity" refer to the degree to which the catalyst is able to catalyze the reactions conducted in the reactor system.

As used in the present disclosure, the terms "catalyst reactivation" and "reactivating the catalyst" refer to processing the deactivated catalyst to restore at least a portion of the catalyst activity to produce a reactivated catalyst. The deactivated catalyst may be reactivated by, but not limited to, recovering catalyst acidity, oxidizing the catalyst, other reactivation process, or combinations thereof.

The catalyst systems and methods for producing olefins of the present disclosure will now be described in the context of an example FCDh system. It should be understood that the schematic diagram of FIG. 1 is only an example system and that other FCDh systems are contemplated as well, and the concepts described may be utilized in such alternate systems. For example, the concepts described may be equally applied to other systems with alternate reactor units and regeneration units, such as those that operate under non-fluidized conditions or are downers rather than risers. Additionally, the presently described catalyst systems and methods for producing olefins should not be limited only to embodiments for reactor systems designed to produce light olefins through FCDh processes, such as the reactor system described with respect to FIG. 1, as other dehydrogenation systems (e.g., utilizing different chemical feeds) are contemplated.

Referring now to FIG. 1, an example reactor system 102 is schematically depicted. The reactor system 102 generally includes a reactor portion 200 and a catalyst-processing portion 300. As used in the context of FIG. 1, the reactor portion 200 refers to the portion of the reactor system 102 in which the major process reaction takes place. For example, the reactor system 102 may be an FCDh system in which a hydrocarbon-containing feed is dehydrogenated in the presence of a dehydrogenation catalyst in the reactor portion 200 of the reactor system 102. The reactor portion 200 generally includes a reactor 202, which may include an upstream reactor section 250, a downstream reactor section 230, and a catalyst separation section 210, which serves to separate catalyst from effluent produced in the reactor 202.

Similarly, as used in the context of FIG. 1, the catalyst-processing portion 300 refers to the portion of the reactor system 102 in which catalyst is processed in some way, such as removal of coke deposits, heating, reactivating, or combinations of these. The catalyst-processing portion 300 generally includes a combustor 350, a riser 330, a catalyst separation section 310, and an oxygen treatment zone 370. The combustor 350 may be in fluid communication with the riser 330. The combustor 350 may also be in fluid communication with the catalyst separation section 210 via standpipe 426, which may supply deactivated catalyst from the reactor portion 200 to the catalyst processing portion 300 for catalyst processing (e.g., coke removal, heating, reactivating, etc.). The oxygen treatment zone 370 may be in fluid communication with the upstream reactor section 250 (e.g., via standpipe 424 and transport riser 430), which may supply processed catalyst from the catalyst processing portion 300 back to the reactor portion 200. The combustor 350 may include one or more lower combustor inlet ports 352 where air inlet 428 connects to the combustor 350. The air inlet 428 may supply air and/or other reactive gases, such as an oxygen-containing gas to the combustor 350. The combustor 350 may also include a fuel inlet 354, which may supply a fuel, such as a hydrocarbon stream, to the combustor 350. The oxygen treatment zone 370 may include an oxygen-containing gas inlet 372, which may supply an oxygen-containing gas to the oxygen treatment zone 370 for oxygen treatment of the catalyst.

Referring still to FIG. 1, general operation of the reactor system 102 to conduct a dehydrogenation reaction under normal operating conditions will be described. During operation of the reactor portion 200 of the reactor system 102, a hydrocarbon-containing feed may enter the reactor portion 200 via feed inlet 434 and contact a fluidized catalyst introduced to the reactor portion 200 via a transport riser 430, and an olefin-containing effluent may exit the reactor portion 200 via pipe 420. In one or more embodiments, the hydrocarbon-containing feed and a fluidized catalyst are introduced into the upstream reactor section 250, the hydrocarbon-containing feed contacts the catalyst in the upstream reactor section 250, and the resulting mixture flows upwardly into and through the downstream reactor section 230 to produce the olefin-containing effluents.

In one or more embodiments, the hydrocarbon-containing feed includes ethane, propane, n-butane, i-butane, ethylbenzene, or combinations of these. In some embodiments, the hydrocarbon-containing feed includes at least 50 weight percent (wt. %), at least 60 wt. %, at least 70 wt. %, at least 80 wt. %, at least 90 wt. %, at least 95 wt. %, or at least 99 wt. % ethane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % propane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of n-butane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of i-butane. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of ethylbenzene. In some embodiments, the hydrocarbon-containing feed includes at least 50 wt. %, at least 60 wt. %, at least 70 wt. %, at least 80 wt. %, at least 90 wt. %, at least 95 wt. %, or at least 99 wt. % of the sum of ethane, propane, n-butane, i-butane, and ethylbenzene.

In one or more embodiments, the olefin-containing effluent includes light olefins. As used in the present disclosure, the term "light olefins" refers to one or more of ethylene, propylene, and butene. The term butene includes any isomers of butene, such as α-butylene, cis-β-butylene, trans-β-butylene, and isobutylene. In some embodiments, the olefin-containing effluent includes at least 25 wt. % light olefins based on the total weight of the olefin-containing effluent. For example, the olefin-containing effluent may include at least 35 wt. % light olefins, at least 45 wt. % light olefins, at least 55 wt. % light olefins, at least 65 wt. % light olefins, or at least 75 wt. % light olefins based on the total weight of the olefin-containing effluent.

In one or more embodiments, the catalyst includes catalytically active particles. In some embodiments, the catalyst includes one or more of gallium, platinum, alkali metals, alkaline earth metals, and a support material.

In one or more embodiments, the catalyst includes from 5 ppm to 500 ppm platinum based on the total weight of the catalyst. For example, the catalyst may include from 5 ppm to 400 ppm, from 5 ppm to 300 ppm, from 5 ppm to 200 ppm, from 5 ppm to 100 ppm, from 100 ppm to 500 ppm, from 100 ppm to 400 ppm, from 100 ppm to 300 ppm, from 100 ppm to 200 ppm, from 200 ppm to 500 ppm, from 200 ppm to 400 ppm, from 200 ppm to 300 ppm, from 300 ppm to 500 ppm, from 300 ppm to 400 ppm, or from 400 ppm to 500 ppm platinum based on the total weight of the catalyst.

In one or more embodiments, the catalyst includes from 0.1 wt. % to 10.0 wt. % gallium based on the total weight of the catalyst. For example, the catalyst may include from 0.1 wt. % to 7.5 wt. %, from 0.1 wt. % to 5.0 wt. %, from 0.1 wt. % to 2.5 wt. %, from 0.1 wt. % to 0.5 wt. %, from 0.5 wt. % to 10.0 wt. %, from 0.5 wt. % to 7.5 wt. %, from 0.5 wt. % to 5.0 wt. %, from 0.5 wt. % to 2.5 wt. %, from 2.5 wt. % to 10.0 wt. %, from 2.5 wt. % to 7.5 wt. %, from 2.5 wt. % to 5.0 wt. %, from 5.0 wt. % to 10.0 wt. %, from 5.0 wt. % to 7.5 wt. %, or from 7.5 wt. % to 10 wt. % gallium based on the total weight of the catalyst.

In one or more embodiments, the catalyst optionally includes less than 5 wt. % alkali metal or alkaline earth metal based on the total weight of the catalyst. For example, the catalyst may include from 0 wt. % to 5 wt. %, from 0 wt. % to 4 wt. %, from 0 wt. % to 3 wt. %, from 0 wt. % to 2 wt. %, from 0 wt. % to 1 wt. %, from 1 wt. % to 5 wt. %, from 1 wt. % to 4 wt. %, from 1 wt. % to 3 wt. %, from 1 wt. % to 2 wt. %, from 2 wt. % to 5 wt. %, from 2 wt. % to 4 wt. %, from 2 wt. % to 3 wt. %, from 3 wt. % to 5 wt. %, from 3 wt. % to 4 wt. %, or from 4 wt. % to 5 wt. % alkali metal or alkaline earth metal based on the total weight of the catalyst.

In one or more embodiments, the catalyst includes a support material. Specifically, the catalyst may include gallium, platinum, alkali metal, and/or alkaline earth metal disposed and/or dispersed on the support material. In some embodiments, the support material includes one or more of alumina, silica, titanium oxide, and zirconium. For example, the support material may include one or more of alumina, silica-containing alumina, titanium oxide-containing alumina, and zirconium-containing alumina.

In one or more embodiments, the catalyst has a median particle size of from 50 µm to 90 µm, as determined via laser diffraction ASTM D4464-15. For example, the catalyst may have a median particle size of from 50 µm to 80 µm, from 50 µm to 70 µm, from 50 µm to 60 µm, from 60 µm to 90 µm, from 60 µm to 80 µm, from 60 µm to 70 µm, from 70 µm to 90 µm, from 70 µm to 80 µm, or from 80 µm to 90 µm, as determined via laser diffraction ASTM D4464-15.

Referring still to FIG. 1, the olefin-containing effluent and the catalyst may be passed out of the downstream reactor section 230 to a separation device 220 in the catalyst separation section 210. The catalyst may be separated from the olefin-containing effluent in the separation device 220. The olefin-containing effluent may then be transported out of the catalyst separation section 210. For example, the separated olefin-containing effluent may be removed from the reactor system 102 via a pipe 420 at a gas outlet port 216 of the catalyst separation section 210. In one or more embodiments, the separation device 220 may be a cyclonic separation system, which may include two or more stages of cyclonic separation.

Referring still to FIG. 1, following separation from the olefin-containing effluent in the separation device 220, the catalyst may generally move through the stripper 224 to the reactor catalyst outlet port 222 where the catalyst may be transferred out of the reactor portion 200 via standpipe 426 and into the combustor 350 of the catalyst-processing portion 300. Optionally, the catalyst may also be transferred directly back into the upstream reactor section 250 via standpipe 422. In one or more embodiments, recycled catalyst from the stripper 224 may be premixed with processed catalyst from the catalyst-processing portion 300 in the transport riser 430.

Once passed to the catalyst-processing portion 300, the catalyst may be processed in the catalyst-processing portion 300. As used in the present disclosure, the term "catalyst processing" refers to preparing the catalyst for re-introduction into the reactor portion of the reactor system. In one or more embodiments, processing the catalyst includes removing coke deposits from the catalyst, raising the temperature of the catalyst through combustion of a combustion fuel, reactivating the catalyst, stripping one or more constituents from the catalyst, or combinations of these.

In some embodiments, processing the catalyst includes combusting the combustion fuel in the presence of the catalyst in the combustor 350 to remove coke deposits on the catalyst and/or heat the catalyst to produce a processed catalyst and combustion gases. As used in the present disclosure, the term "processed catalyst" refers to catalyst that has been processed in the catalyst-processing portion 300 of the reactor system 102. The processed catalyst may be separated from the combustion gases in the catalyst separation portion 310 and, in some embodiments, may then be reactivated by conducting an oxygen treatment of the heated catalyst. The oxygen treatment may include contacting the catalyst with an oxygen-containing gas for a period of time sufficient to reactivate the catalyst.

In one or more embodiments, the combustion fuel includes coke or other contaminants deposited on the catalyst in the reactor portion 200. The catalyst may be coked following the reactions in the reactor portion 200, and the coke may be removed from the catalyst by a combustion reaction in the combustor 350. For example, an oxidizer (such as air) may be fed into the combustor 350 via the air inlet 428. Alternatively or additionally, such as when coke is not formed on the catalyst or an amount of coke formed on the catalyst is not sufficient to burn off to heat the catalyst to a desired temperature, a supplemental fuel may be injected into the combustor 350, which may be burned to heat the catalyst.

The processed catalyst may be passed out of the combustor 350 and through the riser 330 to a riser termination separator 378, where the gas and solid components from the riser 330 may be at least partially separated. The vapor and remaining solids may be transported to a secondary separation device 320 in the catalyst separation section 310 where the remaining processed catalyst is separated from the gases from the catalyst processing (e.g., gases emitted by combustion of coke deposits and supplemental fuel). In some embodiments, the secondary separation device 320 may include one or a plurality of cyclone separation units, which may be arranged in series or in multiple cyclone pairs. The combustion gases from combustion of coke and/or the supplemental fuel during processing of the catalyst or other gases introduced to the catalyst during catalyst processing may be removed from the catalyst-processing portion 300 via a combustion gas outlet 432.

As previously discussed, processing the catalyst in the catalyst processing portion 300 of the reactor system 102 may include reactivating the catalyst. Combustion of a supplemental fuel in the presence of the catalyst to heat the catalyst may further deactivate the catalyst. Accordingly, in some embodiments, the catalyst may be reactivated by conditioning the catalyst through an oxygen treatment. The oxygen treatment to reactivate the catalyst may be conducted after combustion of the supplemental fuel to heat the catalyst. In some embodiments, the oxygen treatment includes treating the processed catalyst with an oxygen-containing gas. The oxygen-containing gas may include an oxygen content of from 5 mole percent (mol. %) to 100 mol. % based on total molar flow rate of the oxygen-containing gas. In some embodiments, the oxygen treatment includes maintaining the processed catalyst at a temperature of at least 660 degrees Celsius (° C.) while exposing the catalyst to a flow of an oxygen-containing gas for a period of time sufficient to reactivate the processed catalyst (e.g., increase the catalytic activity of the processed catalyst).

In one or more embodiments, treatment of the processed catalyst with the oxygen-containing gas is conducted in the oxygen treatment zone 370. In some embodiments, the oxygen treatment zone 370 is downstream of the catalyst separation portion 310 of the catalyst processing portion 300, such that the processed catalyst is separated from the combustion gases before being exposed to the oxygen-containing gas during the oxygen treatment. In some embodiments, the oxygen treatment zone 370 includes a fluid solids contacting device. The fluid solids contacting device may include baffles or grid structures to facilitate contact of the processed catalyst with the oxygen-containing gas. Examples of fluid solid contacting devices are described in further detail in U.S. Pat. Nos. 9,827,543 and 9,815,040.

In one or more embodiments, processing the catalyst in the catalyst-processing portion 300 of the reactor system 102 includes stripping the processed catalyst of molecular oxygen trapped within or between catalyst particles and physisorbed oxygen that is desorbable at a temperature of at least 660° C. The stripping step may include maintaining the processed catalyst at a temperature of at least 660° C. and exposing the processed catalyst to a stripping gas that is substantially free of molecular oxygen and combustible fuels for a period of time sufficient to remove the molecular oxygen from between particles and physisorbed oxygen that is desorbable at the temperature of at least 660° C. Further description of these catalyst reactivation processes are disclosed in U.S. Pat. No. 9,834,496.

Referring still to FIG. 1, following processing of the catalyst, the processed catalyst may be passed from the catalyst-processing portion 300 back into the reactor portion 200 via standpipe 424. For example, the processed catalyst may be passed from the oxygen treatment zone 370 to the upstream reactor section 250 via standpipe 424 and transport riser 430, where the processed catalyst may be further utilized in a dehydrogenation reaction of a hydrocarbon-containing feed. Accordingly, in operation, the catalyst may cycle between the reactor portion 200 and the catalyst-processing portion 300. In general, the processed chemical streams, including the hydrocarbon-containing feed and the olefin-containing effluent may be gaseous, and the catalyst may be a fluidized particulate solid. In one or more embodiments, the reactor system 102 may include a hydrogen inlet stream 480 which provides supplemental hydrogen to the reactor system 102.

As discussed previously, the performance of fluidized bed reactors is greatly dependent on the quality of fluidization of the catalyst. While the catalyst may have a suitable quality of fluidization when first introduced to the reactor system 102, natural attrition of the catalytically active particles of the catalyst and, in particular, the relatively smaller catalytically active particles of the catalyst may result in the degradation of the quality of fluidization of the catalyst over time. In order to improve the quality of fluidization of the catalyst, a fluidization promoter may be introduced to the reactor system 102. In some embodiments, the fluidization promoter is introduced to the reactor system 102 via the reactor portion 200, the catalyst-processing portion 300, or both. For example, the fluidization promoter may be introduced to the reactor system 102 via transport riser 430.

In some embodiments, the fluidization promoter includes catalytically active particles. In some embodiments, the fluidization promoter includes one or more of gallium, platinum, alkali metals, alkaline earth metals, and a support material. In some embodiments, the fluidization promoter may include the similar and/or the same materials as the catalyst. For example, in some embodiments both the catalyst and the fluidization promoter may include gallium and platinum disposed and/or dispersed on an alumina support material.

In one or more embodiments, the fluidization promoter includes from 5 ppm to 500 ppm platinum based on the total weight of the fluidization promoter. For example, the fluidization promoter may include from 5 ppm to 400 ppm, from 5 ppm to 300 ppm, from 5 ppm to 200 ppm, from 5 ppm to 100 ppm, from 100 ppm to 500 ppm, from 100 ppm to 400 ppm, from 100 ppm to 300 ppm, from 100 ppm to 200 ppm, from 200 ppm to 500 ppm, from 200 ppm to 400 ppm, from 200 ppm to 300 ppm, from 300 ppm to 500 ppm, from 300 ppm to 400 ppm, or from 400 ppm to 500 ppm platinum based on the total weight of the fluidization promoter.

In one or more embodiments, the fluidization promoter includes less platinum than the catalyst. In some embodiments, the fluidization promoter may include platinum in an amount of from 40% to 90% of the amount of platinum of the catalyst. For example, the fluidization promoter may include platinum in an amount of from 40% to 90%, from 40% to 80%, from 40% to 70%, from 40% to 60%, from 40% to 50%, from 50% to 90%, from 50% to 80%, from 50% to 70%, from 50% to 60%, from 60% to 90%, from 60% to 80%, from 60% to 70%, from 70% to 90%, from 70% to 80%, or from 80% to 90% of the amount of platinum of the catalyst. Without being bound by any particular theory, it is believed that the relatively smaller catalytically active particles of the fluidization promoter may have a superior retention of accessible platinum when compared to the relatively larger catalytically active particles of the catalyst. That is, the fluidization promoter may retain a greater amount of accessible platinum than the catalyst when subjected to the same reaction process. Accordingly, the fluidization promoter may be loaded with less platinum when compared to the catalyst without diluting the catalytic activity within the reactor system 102.

In one or more embodiments, the fluidization promoter includes from 0.1 wt. % to 10.0 wt. % gallium based on the total weight of the fluidization promoter. For example, the fluidization promoter may include from 0.1 wt. % to 7.5 wt. %, from 0.1 wt. % to 5.0 wt. %, from 0.1 wt. % to 2.5 wt. %, from 0.1 wt. % to 0.5 wt. %, from 0.5 wt. % to 10.0 wt. %, from 0.5 wt. % to 7.5 wt. %, from 0.5 wt. % to 5.0 wt. %, from 0.5 wt. % to 2.5 wt. %, from 2.5 wt. % to 10.0 wt. %, from 2.5 wt. % to 7.5 wt. %, from 2.5 wt. % to 5.0 wt. %, from 5.0 wt. % to 10.0 wt. %, from 5.0 wt. % to 7.5 wt. %, or from 7.5 wt. % to 10 wt. % gallium based on the total weight of the fluidization promoter.

In one or more embodiments, the fluidization promoter optionally includes less than 5 wt. % alkali metal or alkaline earth metal based on the total weight of the fluidization promoter. For example, the fluidization promoter may include from 0 wt. % to 5 wt. %, from 0 wt. % to 4 wt. %, from 0 wt. % to 3 wt. %, from 0 wt. % to 2 wt. %, from 0 wt. % to 1 wt. %, from 1 wt. % to 5 wt. %, from 1 wt. % to 4 wt. %, from 1 wt. % to 3 wt. %, from 1 wt. % to 2 wt. %, from 2 wt. % to 5 wt. %, from 2 wt. % to 4 wt. %, from 2 wt. % to 3 wt. %, from 3 wt. % to 5 wt. %, from 3 wt. % to 4 wt. %, or from 4 wt. % to 5 wt. % alkali metal or alkaline earth metal based on the total weight of the fluidization promoter.

In one or more embodiments, the fluidization promoter includes a support material. Specifically, the fluidization promoter may include gallium, platinum, alkali metal, and/or alkaline earth metal disposed and/or dispersed on the support material. In some embodiments, the support material includes one or more of alumina, silica, titanium oxide, and zirconium. For example, the support material may include one or more of alumina, silica-containing alumina, titanium oxide-containing alumina, and zirconium-containing alumina.

In one or more embodiments, the fluidization promoter has a median particle size of from 20 μm to 50 μm, as determined via laser diffraction ASTM D4464-15. For example, the fluidization promoter may have a median particle size of from 20 μm to 45 μm, from 20 μm to 40 μm, from 20 μm to 35 μm, from 20 μm to 30 μm, from 20 μm to 25 μm, from 25 μm to 50 μm, from 25 μm to 45 μm, from 25 μm to 40 μm, from 25 μm to 35 μm, from 25 μm to 30 μm, from 30 μm to 50 μm, from 30 μm to 45 μm, from 30 μm to 40 μm, from 30 μm to 35 μm, from 35 μm to 50 μm, from 35 µm to 45 µm, from 35 µm to 40 µm, from 40 µm to 50 µm, from 40 µm to 45 µm, or from 45 µm to 50 µm, as determined via laser diffraction ASTM D4464-15.

In one or more embodiments, the fluidization promoter has an average particle density less than or equal to 250% of an average particle density of the catalyst. For example, the fluidization promoter may have an average particle density less than or equal to 225%, less than or equal to 200%, less than or equal to 175%, less than or equal to 150%, less than or equal to 125%, less than or equal to 100%, less than or equal to 75%, or less than or equal to 50% of an average particle density of the catalyst. In some embodiments, the fluidization promoter has an average particle density of from 50% to 250%, from 50% to 225%, from 50% to 200%, from 50% to 175%, from 50% to 150%, from 50% to 125%, from 50% to 100%, from 50% to 75%, from 75% to 250%, from 75% to 225%, from 75% to 200%, from 75% to 175%, from 75% to 150%, from 75% to 125%, from 75% to 100%, from 100% to 250%, from 100% to 225%, from 100% to 200%, from 100% to 175%, from 100% to 150%, from 100% to 125%, from 125% to 250%, from 125% to 225%, from 125% to 200%, from 125% to 175%, from 125% to 150%, from 150% to 250%, from 150% to 225%, from 150% to 200%, from 150% to 175%, from 175% to 250%, from 175% to 225%, from 175% to 200%, from 200% to 250%, from 200% to 225%, or from 225% to 250% of an average particle density of the catalyst.

In one or more embodiments, the amount of the fluidization promoter introduced to the reactor system 102 is from 2 vol. % to 30 vol. % of a sum of a volume of the catalyst and a volume of the fluidization promoter. For example, the amount of the fluidization promoter introduced to the reactor system 102 may be from 2 vol. % to 25 vol. %, from 2 vol. % to 20 vol. %, from 2 vol. % to 15 vol. % to 10 vol. %, from 2 vol. % to 5 vol. %, from 5 vol. % to 30 vol. %, from 5 vol. % to 25 vol. %, from 5 vol. % to 20 vol. %, from 5 vol. % to 15 vol. %, from 5 vol. % to 10 vol. %, from 10 vol. % to 30 vol. %, from 10 vol. % to 25 vol. %, from 10 vol. % to 20 vol. %, from 10 vol. % to 15 vol. %, from 15 vol. % to 30 vol. %, from 15 vol. % to 25 vol. %, from 15 vol. % to 20 vol. %, from 20 vol. % to 30 vol. %, from 20 vol. % to 25 vol. %, or from 25 vol. % to 30 vol. % of a sum of a volume of the catalyst and a volume of the fluidization promoter.

It should be understood that, once introduced to the reactor system 102, the fluidization promoter will mix with the catalyst and, as a result, cycle through the reactor system 102 as discussed previously with regard to the catalyst. In other terms, the introduction of fluidization promoter to the reactor system 102 may produce a catalyst system that is a mixture of the catalyst and fluidization promoter. Additionally, as the catalyst system "ages" during use in the reactor system 102 and/or catalytically active particles are naturally lost due to attrition, the fluidization promoter and the catalyst may become indistinguishable from one another. In this regard, the catalyst system may become functionally equivalent to the original catalyst during operation of the reactor system 102, and fresh fluidization promoter may be again introduced to the reactor system 102. Due to the natural change in properties of the catalyst and fluidization promoter during operation of the reactor system 102, the properties and amounts of fluidization promoter and/or catalyst may refer to the properties and amounts of the fluidization promoter and/or catalyst upon introduction of the fluidization promoter to the reactor system 102.

In some embodiments, the catalyst system may include from 2 vol. % to 30 vol. % of the fluidization promoter. For example, catalyst system may include from 2 vol. % to 25 vol. %, from 2 vol. % to 20 vol. %, from 2 vol. % to 15 vol. %, from 2 vol. % to 10 vol. %, from 2 vol. % to 5 vol. %, from 5 vol. % to 30 vol. %, from 5 vol. % to 25 vol. %, from 5 vol. % to 20 vol. %, from 5 vol. % to 15 vol. %, from 5 vol. % to 10 vol. %, from 10 vol. % to 30 vol. %, from 10 vol. % to 25 vol. %, from 10 vol. % to 20 vol. %, from 10 vol. % to 15 vol. %, from 15 vol. % to 30 vol. %, from 15 vol. % to 25 vol. %, from 15 vol. % to 20 vol. %, from 20 vol. % to 30 vol. %, from 20 vol. % to 25 vol. %, or from 25 vol. % to 30 vol. % of the fluidization promoter. In some embodiments, the catalyst system may include from 70 vol. % to 98 vol. % of the catalyst. For example, catalyst system may include from 70 vol. % to 95 vol. %, from 70 vol. % to 90 vol. %, from 70 vol. % to 85 vol. %, from 70 vol. % to 80 vol. %, from 70 vol. % to 75 vol. %, from 75 vol. % to 98 vol. %, from 75 vol. % to 95 vol. %, from 75 vol. % to 90 vol. %, from 75 vol. % to 85 vol. %, from 75 vol. % to 80 vol. %, from 80 vol. % to 98 vol. %, from 80 vol. % to 95 vol. %, from 80 vol. % to 90 vol. %, from 80 vol. % to 85 vol. %, from 85 vol. % to 98 vol. %, from 85 vol. % to 95 vol. %, from 85 vol. % to 90 vol. %, from 90 vol. % to 98 vol. %, from 90 vol. % to 95 vol. %, or from 95 vol. % to 98 vol. % of the catalyst.

As discussed previously, the fluidization promoter may be introduced to the reactor system 102 to improve the quality of fluidization of the catalyst and/or catalyst system. Accordingly, the fluidization promoter may be introduced to the reactor system 102 when poor fluidization of the catalyst and/or catalyst system occurs. Examples of poor fluidization include channeling, formation of large bubbles of the hydrocarbon-containing feed, slugging, gas bypassing, and significant pressure fluctuations. In one or more embodiments, the improvement of the quality of the fluidization of the catalyst may be quantified by an improvement in the MSER of the catalyst system that is formed upon the introduction of the fluidization promoter to the reactor system 102 compared to the catalyst already present in the reactor system 102. Accordingly, in some embodiments, the catalyst system (i.e., a mixture of the catalyst and the fluidization promoter in the reactor system 102) has an MSER at least 2% greater than the MSER of the catalyst alone. For example, the catalyst system may have an MSER at least 5% greater, at least 10% greater, at least 15% greater, at least 20% greater, at least 25% greater, at least 30% greater, at least 35% greater, at least 40% greater, at least 45% greater, or at least 50% greater, than the MSER of the catalyst alone.

Additionally, as a result of the introduction of the relatively smaller catalytically active particles of the fluidization promoter, the Sauter Mean Diameter of the catalyst system may be less than the Sauter Mean Diameter of the catalyst alone. In some embodiments, the Sauter Mean Diameter of the catalyst system is from 30 µm to 90 µm. For example, the Sauter Mean Diameter of the catalyst system may from 30 µm to 80 µm, from 30 µm to 70 µm, from 30 µm to 60 µm, from 30 µm to 50 µm, from 30 µm to 40 µm, from 40 µm to 90 µm, from 40 µm to 80 µm from 40 µm to 70 µm, from 40 µm to 60 µm, from 40 µm to 50 µm, from 50 µm to 90 µm, from 50 µm to 80 µm, from 50 µm to 70 µm, from 50 µm to 60 µm, from 60 µm to 90 µm, from 60 µm to 80 µm, from 60 µm to 70 µm, from 70 µm to 90 µm, from 70 µm to 80 µm, or from 80 µm to 90 µm.

EXAMPLES

The various embodiments of the present disclosure will be further clarified by the following examples. The examples are illustrative in nature and should not be understood to limit the subject matter of the present disclosure.

Example 1

In Example 1, the effect various catalytically active particles (i.e., catalysts and/or fluidization promoters) have on fluidization of a catalyst system was determined. In this regard, six catalytically active particle samples were prepared. For the purposes of Example 1, the amount of gallium loading of each sample was constant, while the amount of platinum loading, particle size distribution, and particle density of each sample was varied.

Sample A, which is representative of a catalyst, was produced by loading an alumina support material with gallium and platinum via a conventional incipient wetness impregnation method, as described in Marceau et al., *Impregnation and Drying*, SYNTHESIS OF SOLID CATALYSTS 59 (2008). Sample B, which is representative of an aged catalyst, was produced in the same manner as Sample A before being used in a fluidized catalytic dehydrogenation system for nine months. Sample C, which is representative of a fluidization promoter, was produced by first sieving an alumina support material via a dry sieving method with 20 μm and 45 μm sieves in a sieve shaker (commercially available as RO-TAP® RX-29 from W. S. Tyler). The sieved fraction of the alumina support material was then loaded with gallium and platinum in the same manner as Sample A. Sample D was produced by mixing Sample A and Sample C at a ratio of 70:30 by weight. Sample E is a hypothetical example that is identical to Sample C, except has 25% less particle density. Sample F is an experimental catalyst with high density and high fines.

The particle density, total amount of fines (i.e., particles having a diameter of from 20 μm to 45 μm), largest particle diameter ($D_{PEAK}$), median diameter ($D_{50}$), and Sauter Mean Diameter for each sample were determined via Particle Size Distribution (PSD) analysis using a laser diffraction-based particle size analyzer (commercially available as LS 13 320 (with a Universal Liquid Module) from Beckman Coulter) with water as the liquid medium. The results are reported in Table 1.

TABLE 1

| Catalytically Active Particles | Particle Density Index | 20-45 μm Particle Fraction (vol. %) | $D_{PEAK}$ (μm) | $D_{50}$ (μm) | Sauter Mean Diameter (μm) |
|---|---|---|---|---|---|
| Sample A | 1.00 | 17 | 88 | 71 | 22 |
| Sample B | 1.00 | 7 | 80 | 76 | 72 |
| Sample C | 1.00 | 61 | 42 | 41 | 16 |
| Sample D | 1.00 | 30 | 46 | 55 | 20 |
| Sample E | 0.75 | 61 | 42 | 41 | 16 |
| Sample F | 2.11 | 56 | 32 | 29 | 15 |

In order to determine the effectiveness of catalytically active particles to improve the fluidization of a catalyst system, various blends of "aged catalyst" (i.e., Sample B) and "fresh catalyst" were prepared. The total amount of fines (i.e., particles having a diameter of from 20 μm to 45 μm), the Sauter Mean Diameter, and the Maximum Stable Expansion Ratio (MSER) of each catalyst blend were determined via Particle Size Distribution (PSD) analysis using a laser diffraction-based particle size analyzer (commercially available as LS 13 320 (with a Universal Liquid Module) from Beckman Coulter) with water as the liquid medium. However, it should be understood that particles having a diameter less than 20 μm were excluded from the determinations of Sauter Mean Diameter and MSER as few of these particles are capable of being retained in a reactor system for a significant period of time, as discussed previously. The results for each catalyst blend are reported in Table 2.

TABLE 2

| Catalyst Blend | Aged Catalyst (vol. %) | Fresh Catalyst (vol. %) | Type of Fresh Catalyst | Total Amount of Fines (20-45 μm) (vol. %) | Sauter Mean Diameter (μm) | MSER Index |
|---|---|---|---|---|---|---|
| Comparative Sample 1 | 100 | — | — | 7 | 74 | 1.00 |
| Comparative Sample 2 | 90 | 10 | Sample A | 8 | 73 | 1.02 |
| Sample 1 | 90 | 10 | Sample C | 13 | 69 | 1.10 |
| Sample 2 | 90 | 10 | Sample D | 11 | 71 | 1.06 |
| Sample 3 | 90 | 10 | Sample E | 13 | 69 | 1.13 |
| Sample 4 | 90 | 10 | Sample F | 14 | 66 | 1.04 |
| Sample 5 | 80 | 20 | Sample C | 19 | 64 | 1.22 |
| Sample 6 | 70 | 30 | Sample C | 24 | 60 | 1.34 |
| Sample 7 | 80 | 20 | Sample F | 28 | 55 | 1.27 |

Generally, the fluidization of a catalyst system may be considered to be improved when the MSER Index (i.e., the ratio of the MSER of the catalyst blend to the MSER of the aged catalyst alone) increases. Based on this, the addition of Sample A (i.e., fresh catalyst) to the aged catalyst did not significantly improve the fluidization of the catalyst blend, as indicated by a relatively minor increase in the MSER Index. In contrast, the addition of Sample C (i.e., a fluidization promoter) to the aged catalyst improved the fluidization of the catalyst blend significantly, as indicated by 10%, 22%, and 34% increases in the MSER Index. Similar improvements in fluidization was also achieved by the addition of Sample E. While only a marginal improvement was achieved by minor additions (i.e., 10 vol. %) of Sample F, a suitable improvement was obtained by increasing the amount added.

Example 2

In Example 2, the metal retention capacity of various catalytically active particles was determined. In this regard, fluidization promoters having various amounts of platinum loading, relative to a common catalyst, were prepared. The catalyst was prepared in the same manner as Sample A of Example 1. Each fluidization promoter was prepared in the same manner as Sample C of Example 1. Each set of catalytically active particles was then subjected to a "Simulated Platinum Retention Test," which is a lab-simulated aging of catalytically active particles in a large scale fluidized catalytic dehydrogenation system via high-severity treatments. Specifically, the catalytically active particles were subjected to two cycles of treatment. Each cycle included a first heat treatment under air at 850° C. for 48 hours, which simulate the increased temperatures of the system, and a mechanical treatment under an air jet with a jet velocity of 150 feet per second (ft/sec) for 6 hours in a 3-inch jet cup, as described in Cocco et al., *Jet Cup Attrition Testing*, 200 POWDER TECHNOLOGY 224 (2010), which is incorporated by reference in its entirety. The results of the Simulated Platinum Retention Test are reported in Table 3.

TABLE 3

|  | Fresh Material | After Simulated Pt Retention Test |
|---|---|---|
|  | Normalized Pt Concentration | |
| Catalyst | 100 | 48 |
| Fluidization Promoter A | 34 | 20 |
| Fluidization Promoter B | 66 | 35 |
| Fluidization Promoter C | 100 | 64 |

As indicated by the results of Table 3, the fluidization promoters are capable of retaining a greater amount of platinum when compared to the catalyst. Specifically, the Fluidization Promoter C lost approximately 36% of the platinum, while the Catalyst lost 52% of the platinum. Indeed, the fresh Fluidization Promoter B, which included approximately 34% less platinum than the Catalyst, included only approximately 27% less platinum than the Catalyst after the Simulated Platinum Retention Test. Based on this, the results of Table 3 indicate that a fresh fluidization promoter does not need to include the same amount of catalytically active material (e.g., platinum) as a fresh catalyst in order to retain a similar amount of the of catalytically active material during use. Put more simply, the results of Table 3 indicate that less catalytically active material can be loaded onto a fluidization promoter without diluting the catalytic activity of a catalyst system.

The present specification includes numerous aspects. One aspect is a fluidization promoter useful for dehydrogenation, the fluidization promoter comprising: from 0.1 weight percent to 10 weight percent gallium based on the total weight of the fluidization promoter; from 5 parts per million to 500 parts per million platinum based on the total weight of the fluidization promoter; less than 5 weight percent of alkali metal or alkaline earth metal based on the total weight of the fluidization promoter; and a support material, wherein a median particle size of the fluidization promoter is from 20 microns to 50 microns.

Another aspect is a catalyst system useful for dehydrogenation, the catalyst system comprising: from 70 volume percent to 98 volume percent of a catalyst having a median particle size of from 50 microns to 90 microns, the catalyst comprising platinum, gallium, and a support material; and from 2 volume percent to 30 volume percent of a fluidization promoter having a median particle size of from 20 microns to 50 microns, the fluidization promoter comprising platinum, gallium, and a support material, wherein the fluidization promoter comprises less platinum than the catalyst.

Another aspect is any other aspect, wherein the catalyst comprises from 0.1 weight percent to 10 weight percent gallium based on the total weight of the catalyst.

Another aspect is any other aspect, wherein the catalyst comprises from 5 parts per million to 500 parts per million of platinum based on the total weight of the catalyst.

Another aspect is any other aspect, wherein the support material of the catalyst comprises alumina, silica, titanium oxide, or zirconium.

Another aspect is any other aspect, wherein the catalyst further comprises less than or equal to 5 weight percent alkali metal or alkaline earth metal based on the total weight of the catalyst.

Another aspect is any other aspect, wherein the fluidization promoter comprises from 0.1 weight percent to 10 weight percent gallium based on the total weight of the fluidization promoter.

Another aspect is any other aspect, wherein the fluidization promoter comprises from 5 parts per million to 500 parts per million of platinum based on the total weight of the fluidization promoter.

Another aspect is any other aspect, wherein the fluidization promoter comprises platinum in an amount of from 40 percent to 90 percent of the amount of platinum of the catalyst.

Another aspect is any other aspect, wherein the support material of the fluidization promoter comprises alumina, silica, titanium oxide, or zirconium.

Another aspect is any other aspect, wherein the fluidization promoter further comprises less than or equal to 5 weight percent alkali metal or alkaline earth metal based on the total weight of the fluidization promoter.

Another aspect is any other aspect, wherein a Sauter Mean Diameter of the catalyst system is from 30 microns to 90 microns.

Another aspect is a method for producing olefins, the method comprising: contacting a hydrocarbon-containing feed with a catalyst in a reactor portion of a reactor system to form an olefin-containing effluent; separating at least a portion of the olefin-containing effluent from the catalyst; passing the catalyst to a catalyst-processing portion of the reactor system and processing the catalyst to produce a processed catalyst; passing the processed catalyst from the catalyst processing portion to the reactor portion; and introducing a fluidization promoter to the reactor system such that a quality of fluidization of the catalyst is improved, wherein: the catalyst has a median particle size of from 50 microns to 90 microns and comprises platinum, gallium, and a support material; the fluidization promoter has a median particle size of from 20 microns to 50 microns and comprises platinum, gallium, and a support material; and the fluidization promoter comprises less platinum than the catalyst.

Another aspect is any other aspect, wherein the fluidization promoter comprises platinum in an amount of from 40 percent to 90 percent of the amount of platinum of the catalyst.

Another aspect is any other aspect, wherein an amount of the fluidization promoter introduced to the reactor system is from 2 volume percent to 30 volume percent of a sum of a volume of the catalyst and a volume of the fluidization promoter.

The dimensions and values presently disclosed are not to be understood as being strictly limited to the exact numerical values recited. Instead, unless otherwise specified, each such dimension or value is intended to mean both the recited value and a functionally equivalent range surrounding that value. For example, a value disclosed as "150 ppmw" is intended to mean "about 150 ppmw."

Every document cited in the present disclosure, if any, including any cross-referenced or related patent or patent application, and any patent or patent application to which this application claims priority or benefit, is incorporated by reference in its entirety unless expressly excluded or otherwise limited. The citation of any document is not an admission that it is prior art with respect to any embodiment disclosed or claimed, or that it alone, or in any combination with any other reference or references, teaches, suggests, or discloses any such embodiment. Further, to the extent that any meaning or definition of a term in this document conflicts with any meaning or definition of the same term in a document incorporated by reference, the meaning or definition assigned to that term in this document governs.

It is noted that one or more of the following claims utilize the term "wherein" as a transitional phrase. For the purposes of defining the embodiments of the present disclosure, it is noted that this term is introduced in the claims as an open-ended transitional phrase that is used to introduce a recitation of a series of characteristics of the embodiment and should be interpreted in like manner as the more commonly used open-ended preamble term "comprising."

It will be apparent to those skilled in the art that various modifications and variations can be made to the presently disclosed embodiments without departing from the scope of the present disclosure. Since modifications, combinations, sub-combinations, and variations of the presently disclosed embodiments incorporating the scope of the present disclosure may occur to persons of ordinary skill in the art, the present disclosure should be construed to include everything within the scope of the appended claims and their equivalents.

The invention claimed is:

1. A fluidization promoter useful for dehydrogenation, the fluidization promoter comprising:
   from 0.1 weight percent to 10 weight percent gallium based on the total weight of the fluidization promoter;
   from 5 parts per million to 500 parts per million platinum based on the total weight of the fluidization promoter;
   less than 5 weight percent of alkali metal or alkaline earth metal based on the total weight of the fluidization promoter; and
   a support material,
   wherein a median particle size of the fluidization promoter is from 20 microns to 50 microns.

2. A catalyst system useful for dehydrogenation, the catalyst system comprising:
   from 70 volume percent to 98 volume percent of a catalyst having a median particle size of from 50 microns to 90 microns, the catalyst comprising platinum, gallium, and a support material; and
   from 2 volume percent to 30 volume percent of a fluidization promoter having a median particle size of from 20 microns to 50 microns, the fluidization promoter comprising platinum, gallium, and a support material, wherein the fluidization promoter comprises less platinum than the catalyst.

3. The catalyst system of claim 2, wherein the catalyst comprises from 0.1 weight percent to 10 weight percent gallium based on the total weight of the catalyst.

4. The catalyst system of claim 2, wherein the catalyst comprises from 5 parts per million to 500 parts per million of platinum based on the total weight of the catalyst.

5. The catalyst system of claim 2, wherein the support material of the catalyst comprises alumina, silica, titanium oxide, or zirconium.

6. The catalyst system of claim 2, wherein the catalyst further comprises less than or equal to 5 weight percent alkali metal or alkaline earth metal based on the total weight of the catalyst.

7. The catalyst system of claim 2, wherein the fluidization promoter comprises from 0.1 weight percent to 10 weight percent gallium based on the total weight of the fluidization promoter.

8. The catalyst system of claim 2, wherein the fluidization promoter comprises from 5 parts per million to 500 parts per million of platinum based on the total weight of the fluidization promoter.

9. The catalyst system of claim 2, wherein the fluidization promoter comprises platinum in an amount of from 40 percent to 90 percent of the amount of platinum of the catalyst.

10. The catalyst system of claim 2, wherein the support material of the fluidization promoter comprises alumina, silica, titanium oxide, or zirconium.

11. The catalyst system of claim 2, wherein the fluidization promoter further comprises less than or equal to 5 weight percent alkali metal or alkaline earth metal based on the total weight of the fluidization promoter.

12. The catalyst system of claim 2, wherein a Sauter Mean Diameter of the catalyst system is from 30 microns to 90 microns.

13. A method for producing olefins, the method comprising:
   contacting a hydrocarbon-containing feed with a catalyst in a reactor portion of a reactor system to form an olefin-containing effluent;
   separating at least a portion of the olefin-containing effluent from the catalyst;
   passing the catalyst to a catalyst-processing portion of the reactor system and processing the catalyst to produce a processed catalyst;
   passing the processed catalyst from the catalyst processing portion to the reactor portion; and
   introducing a fluidization promoter to the reactor system such that a quality of fluidization of the catalyst is improved, wherein:
   the catalyst has a median particle size of from 50 microns to 90 microns and comprises platinum, gallium, and a support material;
   the fluidization promoter has a median particle size of from 20 microns to 50 microns and comprises platinum, gallium, and a support material; and
   the fluidization promoter comprises less platinum than the catalyst.

14. The method of claim 13, wherein the fluidization promoter comprises platinum in an amount of from 40 percent to 90 percent of the amount of platinum of the catalyst.

15. The method of claim 13, wherein an amount of the fluidization promoter introduced to the reactor system is from 2 volume percent to 30 volume percent of a sum of a volume of the catalyst and a volume of the fluidization promoter.

* * * * *